(12) United States Patent
Beck

(10) Patent No.: US 8,066,635 B2
(45) Date of Patent: Nov. 29, 2011

(54) SPECULUM

(75) Inventor: C. Joseph Beck, Wichita, KS (US)

(73) Assignee: THB Precision, LLC, Wichita, KS (US)

( * ) Notice: Subject to any disclaimer, the term of this patent is extended or adjusted under 35 U.S.C. 154(b) by 761 days.

(21) Appl. No.: 12/042,803

(22) Filed: Mar. 5, 2008

(65) Prior Publication Data

US 2009/0227846 A1   Sep. 10, 2009

(51) Int. Cl.
*A61B 1/32* (2006.01)

(52) U.S. Cl. ........................................ 600/236

(58) Field of Classification Search ........... 600/184–246
See application file for complete search history.

(56) References Cited

U.S. PATENT DOCUMENTS

| | | |
|---|---|---|
| 5,341,798 A | 8/1994 | Grounauer |
| 5,433,190 A | 7/1995 | Sunalp |
| 5,441,040 A | 8/1995 | Williams, Jr. |
| 5,618,261 A | 4/1997 | Nevyas |
| 6,440,065 B1 | 8/2002 | Hered |
| 6,544,169 B2 | 4/2003 | Putrino et al. |
| D498,531 S | 11/2004 | Sinding |
| D500,360 S | 12/2004 | Sinding |
| D505,203 S | 5/2005 | Sinding |
| 7,175,594 B2 | 2/2007 | Foulkes |
| 2002/0103421 A1 | 8/2002 | Putrino et al. |
| 2003/0093113 A1 | 5/2003 | Fogarty et al. |
| 2006/0234187 A1* | 10/2006 | Kilcher et al. ............. 433/140 |
| 2007/0088352 A1 | 4/2007 | Rosen |
| 2007/0270657 A1 | 11/2007 | Stephenson et al. |

* cited by examiner

*Primary Examiner* — Eduardo C Robert
*Assistant Examiner* — Summer Kostelnik
(74) *Attorney, Agent, or Firm* — Standley Law Group LLP

(57) ABSTRACT

A speculum having a generally U-shaped frame with a pair of arms, each arm having a free end, a pair of cups, each cup coupled with the free end of one of the arms, and a pair of surfaces, each surface coupled with one of the cups and having a portion extending upward at an angle from the frame.

20 Claims, 3 Drawing Sheets

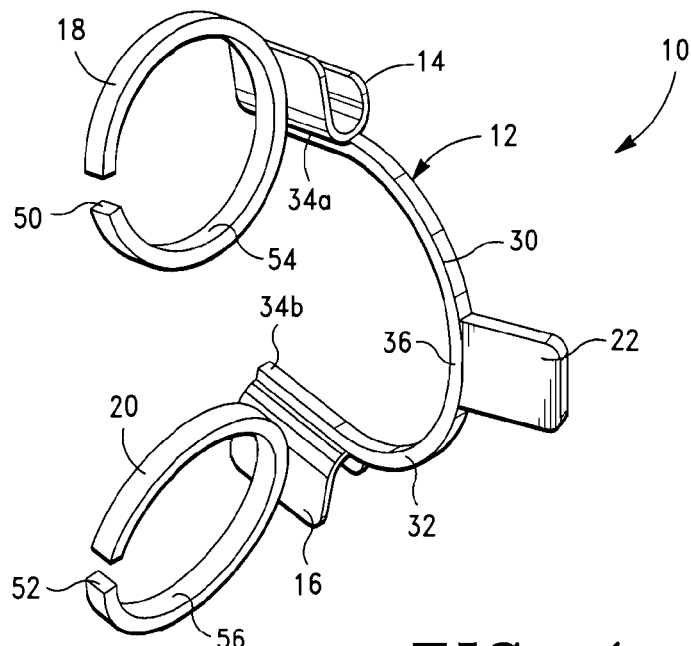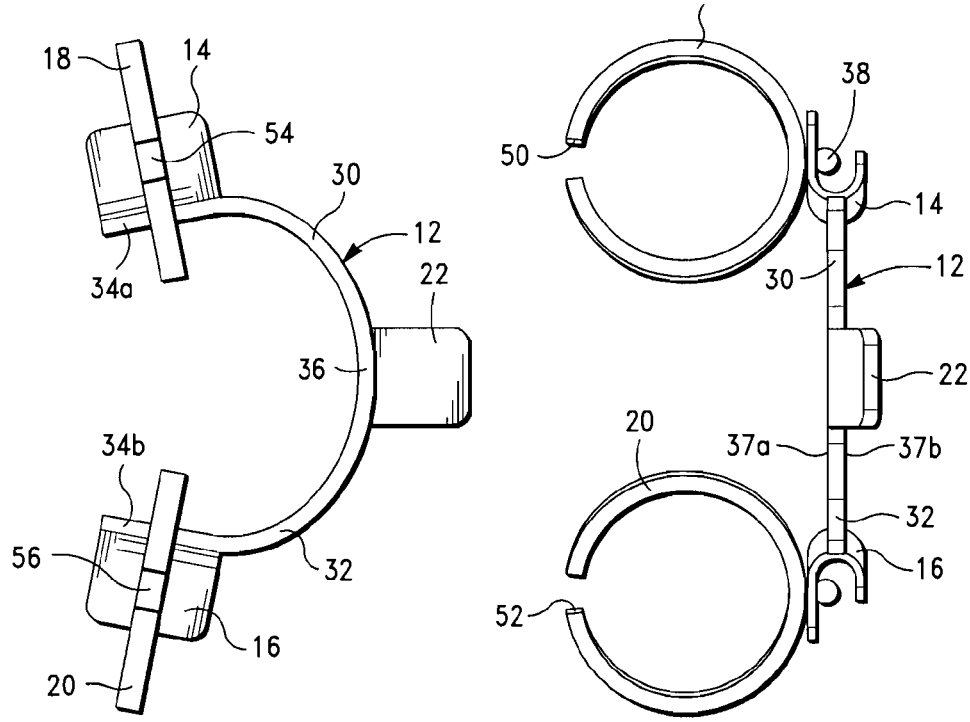

SPECULUM

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Field of the Invention

The present invention relates generally to a speculum, and more particularly to a speculum for retracting the marginal edge portions of a body cavity or opening and providing enhanced access to the retracted area.

2. Description of Related Art

A speculum retracts the marginal edge portions of a body cavity or opening to dilate the opening and provide enhanced access to the underlying anatomic structures. An eyelid speculum retracts the upper and lower eyelids surrounding an eyeball to provide access to the eyeball for examination or performance of a surgical procedure.

One type of eyelid speculum is formed from a loop of wire and has an upper portion that engages an upper eyelid and a lower portion that engages a lower eyelid. The upper and lower portions spread apart to retract the eyelids and expose the eyeball. Because this type of speculum is formed from a loop of wire it only applies force to a small area of each upper and lower eyelid, thus increasing the potential for injury to the eyelids. This type of speculum also does not prevent the eyelashes from contacting the exposed portion of the eyeball, which is a well known cause of infection during eye surgery. The wire loop speculum retracts the midportion of the eyelids for access to the cornea and anterior chamber of the eyeball. The speculum does not retract the eyelids along the temporal or nasal side of the eye cavity. When injecting a pharmaceutical into an eyeball, it is desirable to inject the pharmaceutical into the inferotemporal region of the pars plana in order to avoid damage to the lens or retina. To insert the needle into the inferotemporal region of the pars plana, the temporal side of the lower eyelid must be retracted. A conventional wire loop eyelid speculum does not retract the temporal side of the lower eyelid for injecting a pharmaceutical into the inferotemporal region of the pars plana.

BRIEF SUMMARY OF THE INVENTION

The speculum according to the present invention comprises a pair of arms, each arm comprising a free first end, a pair of cups, each cup coupled with the first end of one of the arms, and a pair of surfaces, each surface having a portion extending upward at an angle from the pair of arms. The surfaces may be joined with either the pair of arms or the cups. Preferably, the speculum exposes a desired portion of an eyeball by positioning each cup around corresponding portions of an upper or lower eyelid and manipulating the surfaces to retract the eyelids, however, the speculum may be used to dilate any opening.

In another embodiment, the present invention is an eyelid speculum comprising an elastic, generally U-shaped frame having a top positioned in a primary speculum plane, a bottom adapted to be positioned adjacent the eyeball, and a pair of free ends. The speculum has a pair of cups, each cup is coupled with a corresponding free end, and a pair of projections, each projection coupled with a corresponding cup. Each projection extends upward from the top of the frame such that the projection is configured to receive a force in a direction that is outside of the primary speculum plane.

In either embodiment, the surfaces or projections are preferably rings extending upward from the frame, or pair of arms, and the rings are configured to receive a person's finger or thumb for manipulating the speculum into a desired location around the eyelids. Preferably, an imaginary plane bisects each ring and is perpendicular to an imaginary plane containing the top surface of the frame. The surfaces or projections may also be any other shape extending upward from the frame. The speculum is also preferably disposable.

The preferred mode of operating the speculum according to the present invention comprises squeezing the surfaces, or projections, together to reduce the distance between the cups and positioning one of the cups around an upper eyelid and the other cup around a lower eyelid. The surfaces or projections may then be released and/or receive a force applied thereto to increase the distance between the cups and the upper and lower eyelids and expose a desired portion of the eyeball. Preferably, the distance between the cups and position of the cups corresponds with a desirable location between the upper and lower eyelids for performing a surgical procedure on the eyeball. The arms are also preferably made from an elastic material so they can be pushed outwardly to further increase the distance between the cups and expose more of the eyeball. In addition, the arms can be manipulated independent of one another such that the lower arm, for example, can be forced to further retract and expose a larger portion of the eyeball while maintaining the upper arm in a fixed position.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

BRIEF DESCRIPTION OF THE DRAWINGS

FIG. 1 is a perspective view of a speculum according to one embodiment of the present invention;

FIG. 2 is a top plan view of the speculum of FIG. 1;

FIG. 3 is a side elevational view of the speculum of FIG. 1;

DETAILED DESCRIPTION OF PREFERRED EMBODIMENT

Figure 4:
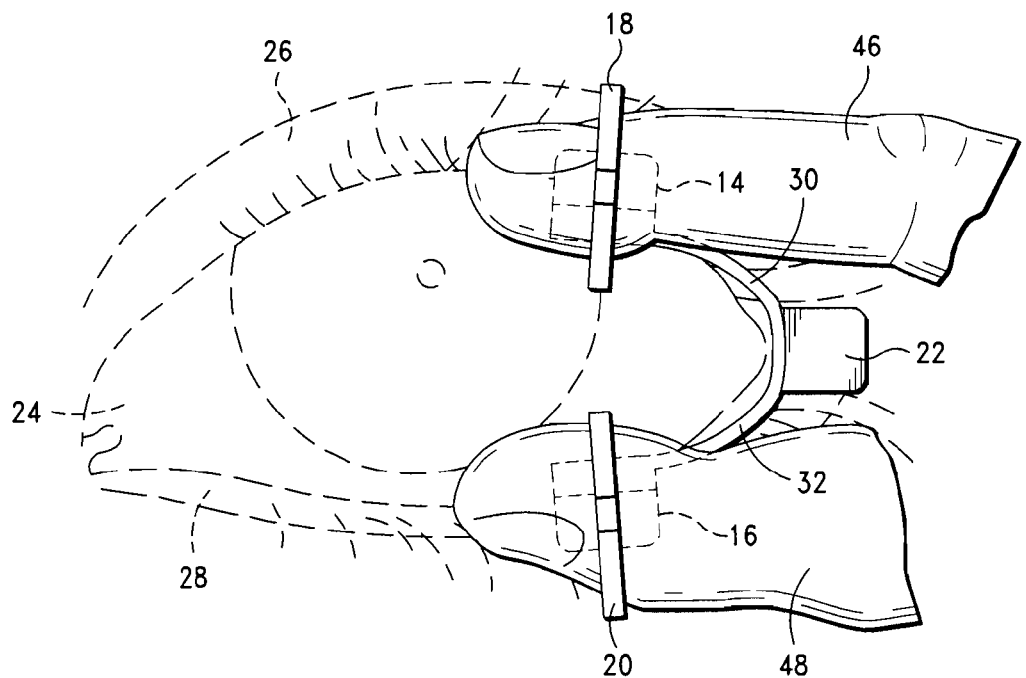
FIG. 4 is a top plan view of the speculum of FIG. 1 retracting upper and lower

Referring now to FIG. 1, a speculum in accordance with one embodiment of the present invention is indicated generally as 10. The speculum has a generally U-shaped frame 12, first and second cups 14 and 16 rigidly joined with the frame, first and second rings 18 and 20 removably joined with first and second cups 14 and 16 and extending upward from frame 12, and a tab 22 rigidly joined with frame 12. As shown in FIG. 4, the speculum exposes a desired portion of an eyeball 24 by retracting the upper and lower eyelids 26 and 28 surrounding the eyeball. Although speculum 10 is shown retracting upper and lower eyelids, the speculum may be used to retract the marginal edges surrounding any body cavity or opening. Additionally, the speculum may either be disposable or reusable after sterilization.

Referring now to FIGS. 1-3, U-shaped frame 12 has first and second arms 30 and 32. Arms 30 and 32 have free first ends 34a and 34b, respectively, and are joined at a central base 36. As shown in FIG. 3, frame 12 has a top 37a and a bottom 37b that is adjacent eyeball 24 when the speculum is in use (shown in FIG. 4). The top 37a of frame 12 is positioned in a primary speculum plane, which is represented by the line A-A in FIG. 6. The distance between first ends 34a and 34b preferably ranges between 30 to 40 millimeters and is most preferably about 35 millimeters, although it is within the scope of the invention for the distance between the ends to be any length. The distance between each of first ends 34a and 34b and base 36 preferably ranges between 20 to 30 millimeters and is most preferably about 25 millimeters, although it is within the scope of the invention for this distance to be any length. Frame 12 preferably has a square cross section with a length and width of approximately two millimeters. Although frame 12 is shown with a square cross section, the cross section of the frame may be any shape. For example, frame 12 may have a circular, triangular, rectangular or trapezoidal cross section. Frame 12 is preferably made from an elastic material such that arms 30 and 32 return to their original shape when no pressure is applied to the arms. Preferably, each arm 30 and 32 may be moved independently such that when the speculum is in use one side of an opening may be retracted farther than the other. The frame is preferably constructed from an inexpensive synthetic polymeric inert material such as polyethylene, polypropylene, polyvinylchloride, acrylic butadiene styrene, nylon, polystyrene or polyurethane, but the frame may be constructed from any material including steel, stainless steel, aluminum or titanium.

First and second cups 14 and 16 are rigidly joined with the first ends 34a, 34b of arms 30 and 32, respectively. The first and second cups may be formed integrally with frame 12 or they may be joined to the frame with fasteners, adhesive, or by a thermal bonding technique such as brazing, soldering, or oxyfuel gas, resistance, electric arc, hot wire, hot gas or infrared welding. Each cup 14 and 16 has a generally U-shaped cross-section when viewed in the respective plane represented by the line B-B or C-C shown in FIG. 5. For each cup, the distance or gap between the two "legs" of the U preferably corresponds with a desirable distance for receiving an upper or lower eyelid as shown in FIG. 4. For an adult person this distance is approximately between three to five millimeters, and most preferably is about four millimeters. The dimensions of each cup when viewed from the top, as shown in FIGS. 2 and 4, are preferably sized to contain the eyelashes on the upper and lower eyelids when in use, thus preventing the eyelashes from contacting the eyeball in the region exposed by the speculum. Preferably, when viewed from the top, as shown in FIG. 2, each cup 14 and 16 extends approximately 10 millimeters away from the respective leg 30, 32 and each cup extends approximately 12 millimeters from the respective first end 34a, 34b toward base 36. The two "legs" of the U of each cup 14 and 16 preferably extend different distances from frame 12, as shown in FIGS. 1 and 3.

While the length of the "leg" of each cup 14 and 16 that rests on the outer surface of the respective upper or lower eyelid, as shown in FIG. 4, is approximately 10 millimeters, the "leg" which fits inside the eye cavity preferably has a length of approximately 5 millimeters. It should be understood that the preferable cup dimensions disclosed above are not essential to the invention and that the cups may have any dimensions. For example, the cups are preferably smaller for retracting the eyelids of children. The cups may also be sized such that they are configured to retract the marginal edge portions of other body cavities or openings. The cups are preferably made from the same material as the frame, but it is within the scope of the invention for the cups to be made from a different material than the frame.

Figures 5, 6:
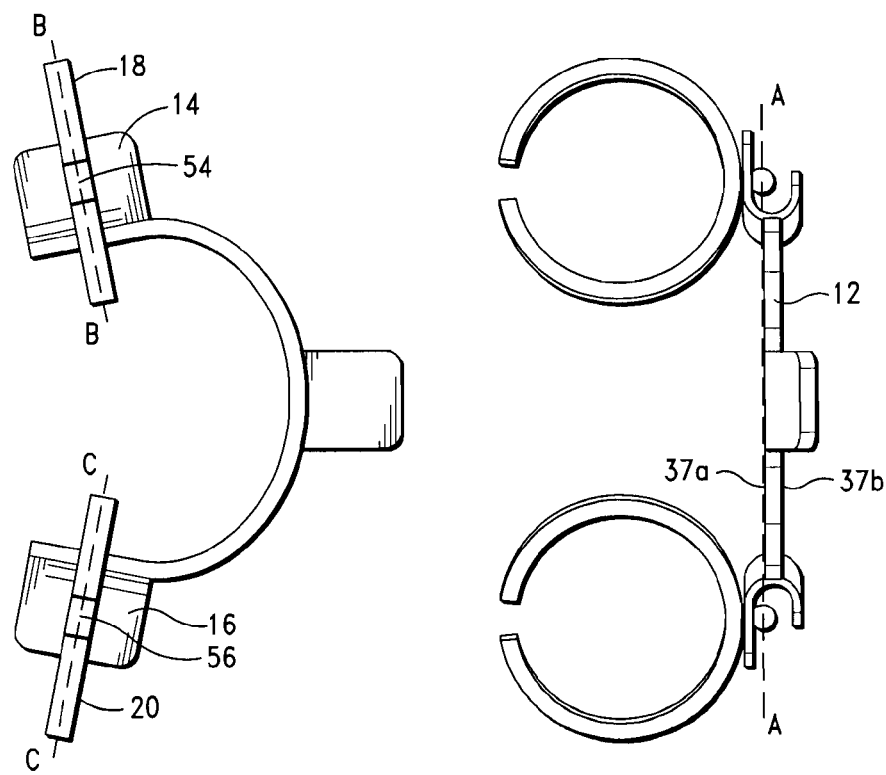
FIG. 5 is a top plan view of the speculum of FIG. 1, showing lines B-B and C-C representing imaginary planes that bisect each ring respectively.
FIG. 6 is a side elevational view of the speculum of FIG. 1, showing line A-A representing an imaginary plane in which the top surface of speculum extends.

Referring now to FIGS. 1-4, each ring 18 and 20 extends upward from the top 37a of frame 12 such that the ring is configured to receive a force in a direction that is outside of the primary speculum plane represented by the line A-A in FIG. 6. In this manner, a user can freely access and manipulate the speculum via the rings in a position above and remote from the eye area. Each ring 18 and 20 preferably has an interior diameter which is slightly larger than an index finger 46 and a thumb 48, respectively. Preferably, the interior diameter of each ring is between 15 to 25 millimeters and most preferably the diameter is about 20 millimeters. Each ring 18 and 20 also has a gap 50 and 52, respectively, at the top of the ring so that the ring is expandable to accommodate a larger finger or thumb. Each ring 18 and 20 has an interior surface 54 and 56, respectively, which is generally annular except for the respective gap 50, 52. A majority of each annular surface 54 and 56 extends upward at an angle from arms 30 and 32.

As shown in FIG. 4, finger 46 is in contact with the interior surface of ring 18 and thumb 48 is in contact with the interior surface of ring 20. Finger 46 and thumb 48 are in contact with surfaces 54 and 56 (shown in FIG. 1) for manipulating the position of cups 14 and 16. Surfaces 54 and 56 may be squeezed toward each other to reduce the distance between cups 14 and 16. Surfaces 54 and 56 may also be spread apart to increase the distance between cups 14 and 16. Finger 46 and thumb 48 may also move the entire frame 12 by applying a force to the respective surface 54 and 56.

Although surfaces 54 and 56 are generally annular, it is within the scope of the invention for the surfaces to have any shape. For instance, the surfaces could be rectangular or trapezoidal. Although rings 18 and 20, and their respective surfaces 54 and 56, are removably joined with cups 14 and 16, it is within the scope of the invention for the rings to be either removably or rigidly joined with either the arms or the cups. Each ring is preferably made from the same material as frame 12, however, it is within the scope of the invention for the rings to be made from a different material.

Figure 7:
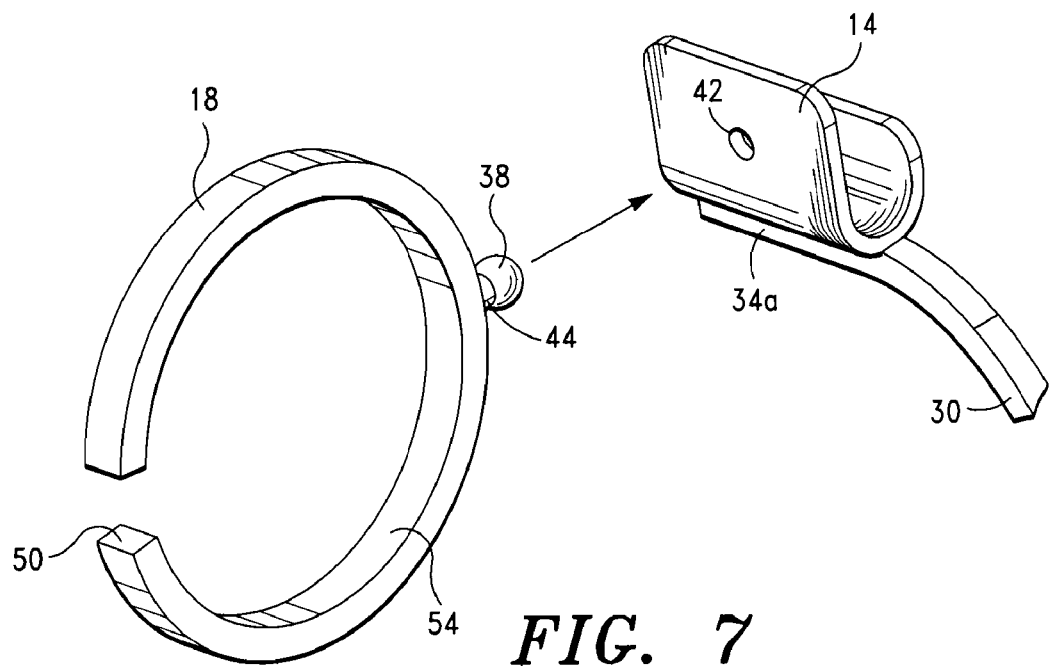
FIG. 7 is a fragmentary exploded perspective view of the speculum of FIG. 1.

Because first and second rings 18 and 20 are substantially identical, the rings will be described herein with reference to only first ring 18, as shown in FIG. 7. Ring 18 is configured to be removably joined with cup 14 via a spherical ball 38 which is received by an opening 42 in cup 14. Ball 38 preferably has a diameter that is slightly larger than opening 42 so the ball is retained within the cup after it is pressed through the opening. Ball 38 preferably has a diameter of approximately 2 millimeters, although it is within the scope of the invention for the ball to have a different diameter. Ball 38 is joined with ring 18 by a post 44. Post 44 is received by opening 42 after ball 38 is pressed through the opening. Post 44 preferably has a diameter which is slightly smaller than the diameter of the opening such that the post can rotate with respect to the cup 14.

Preferably, the post has a diameter of approximately 1.5 millimeters, although it is within the scope of the invention for the post to have a different diameter. Opening 42 preferably has a diameter of between 1.5 to 2 millimeters, although it is within the scope of the invention for the opening to have a different diameter. There may also be more than one opening in cup 14 for positioning ring 18 at different locations on the cup.

Referring now to FIGS. 1-3, tab 22 extends outwardly from frame 12 adjacent base 36 at an angle from the top 37a of frame 12. Tab 22 extends downward at an angle from the top 37a of frame 12 to enhance access to the area retracted by the speculum. Tab 22 preferably extends downward from the top of the frame at an angle that matches the slope of a face from the corner of the eye opening to the temple, as shown in FIG. 4. Preferably, tab 22 extends downward at an approximately 20 degree angle from the top 37a of frame 12, although it is within the scope of the invention for the tab to be parallel to top 37a, or to extend upward or downward at any angle from the top of the frame.

Referring now to FIG. 6, line A-A represents the primary speculum plane which is an imaginary plane in which the top surface 37a of frame 12 is positioned. Referring to FIG. 5, line B-B represents both a first cup plane, which bisects cup 14, and a first surface plane, which bisects surface 54 and ring 18 such that there is a ring of equal thickness on each side of the surface plane. Line C-C represents both a second cup plane, which bisects cup 16, and a second surface plane, which bisects surface 56 and ring 20 such that there is a ring of equal thickness on each side of the surface plane. Each of the cup planes and the surface planes are perpendicular to the primary speculum plane, but it is within the scope of the invention for the cup planes and the surface planes to be positioned at any angle with respect to the primary speculum plane. Although the surface plane and cup plane represented by line B-B are aligned, it is within the scope of the invention for the planes to not be aligned. For instance, ring 18 could be rotated with respect to cup 14, or the ring could be coupled with the cup in a different location than that shown in FIG. 5. It is also within the scope of the invention for the surface plane and cup plane represented by line C-C to not be aligned.

Figure 8:
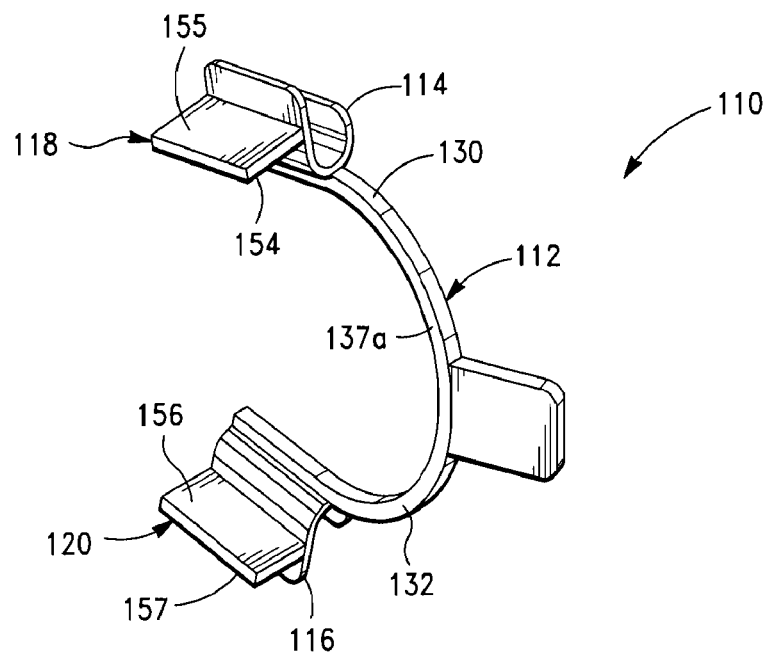
FIG. 8 is a perspective view of an alternative embodiment of a speculum according to the present invention.

Referring now to FIG. 8, an alternative embodiment of a speculum according to the present invention is indicated generally as 110. Speculum 110 is substantially similar to speculum 10, shown in FIGS. 1-7, except that the projections 118 and 120 on speculum 110 are rectangular plates instead of rings. Each projection 118 and 120 is joined with the respective cup 114 and 116 in the same manner as described above for the ring and cup of speculum 10. Each projection has a rectangular surface 154 and 156 extending upward at an angle from frame 112. Surfaces 154 and 156 are generally perpendicular to the top 137a of frame 112, although it is within the scope of the invention for the surfaces to be positioned at any angle with respect to the top of the frame. Surfaces 154 and 156 are positioned to receive a force with a direction that is above and parallel to the top of the frame for manipulating arms 130 and 132. Thus, the user can manipulate the surfaces in a position remote from the eye area.

Referring now to FIG. 4, in use, finger 46 is inserted into ring 18 of speculum 10 and thumb 48 is inserted into ring 20. Rings 18 and 20 are squeezed toward each other to reduce the distance between cups 14 and 16. Cup 14 is positioned around upper eyelid 26 and cup 16 is positioned around lower eyelid 28. Interior surfaces 54 and 56 (shown in FIG. 1) of rings 18 and 20 are manipulated to move cups 14 and 16 over the desired portion of the eyelids. Tab 22 may also be used to move the frame and position the cups 14 and 16 over the desired portion of the eyelids. Finger 46 and thumb 48 release pressure from surfaces 54 and 56 to increase the distance between cups 14 and 16. Cups 14 and 16 retract upper and lower eyelids 26 and 28 as the distance between the cups increases, thus exposing a desired portion of the eyeball. Thumb 48 pushes ring 20 and surface 56 (shown in FIG. 1) downward to retract lower eyelid 28 and expose the majority of the anterior side of the inferotemporal quadrant of the eyeball (the lower right portion of the front of the eyeball shown in FIG. 4). After lower eyelid 28 is retracted, a needle (not shown) may be inserted into the eyeball to inject a pharmaceutical into the eyeball. Preferably, the needle is inserted into the inferotemporal region of the pars plana of the eyeball to avoid injury to the lens and retina.

Although the speculum is shown exposing the anterior side of the inferotemporal quadrant, it is within the scope of the invention for the speculum to expose the anterior side of the other three quadrants of the eyeball. For instance, the superotemporal quadrant (the upper right quadrant of the eyeball shown in FIG. 4) may be exposed by pushing ring 18 and surface 54 upward with finger 46 to retract upper eyelid 26. The inferonasal quadrant (the lower left quadrant of the eyeball shown in FIG. 4) and the superonasal quadrant (the upper left quadrant of the eyeball shown in FIG. 4), may be exposed by first positioning cup 14 around the nasal side of lower eyelid 28 and cup 16 around the nasal side of upper eyelid 26. To expose the superonasal quadrant of the eyeball, thumb 48 pushes ring 20 and surface 56 upward retracting upper eyelid 26. To expose the inferonasal quadrant of the eyeball, finger 46 pushes ring 18 and surface 54 downward retracting lower eyelid 28. The speculum may also be used to expose the anterior chamber of the eyeball.

Speculum 110, shown in FIG. 8, operates similarly to speculum 10, described above except that the index finger is positioned adjacent surface 154 and the thumb is positioned adjacent surface 156 for manipulating arms 130 and 132 and frame 112. Speculum 110 otherwise operates in the same manner as speculum 10.

Thus, each of speculums 10 and 110 may retract upper and lower eyelids to expose the anterior side of any portion of an eyeball. The interior surfaces 54 and 56 of rings 18 and 20, and surfaces 154 and 156 of projections 118 and 120, enable the speculum to be easily maneuvered to expose any portion of an eyeball. Cups 14, 16, 114 and 116 are sized to contain the eyelashes in order to prevent the eyelashes from contacting the exposed portion of the eyeball, which reduces the likelihood of infection when performing a surgical procedure on the eyeball.

From the foregoing it will be seen that this invention is one well adapted to attain all ends and objectives herein-above set forth, together with the other advantages which are obvious and which are inherent to the invention.

Since many possible embodiments may be made of the invention without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. A speculum, comprising:
a pair of arms, each arm comprising a free first end and placed within a primary speculum plane;
a pair of cups, each cup coupled with a corresponding first end of one of said arms; and
a pair of projections, each projection coupled with a corresponding one of said cups and extending primarily upward and away from the primary speculum plane.

2. The speculum of claim 1, wherein each of said projections is generally annular.

3. The speculum of claim 2, wherein each of a pair of projection planes bisects one of said generally annular projections such that there is a generally annular projection on each side of said projection plane, and wherein each of said projection planes is positioned at an angle to said primary speculum plane.

4. The speculum of claim 3, wherein each of a pair of cup planes bisects one of said cups, wherein each of said cups comprises a generally U-shaped cross section when viewed in said bisecting cup plane, and wherein each cup plane is positioned at an angle to said primary speculum plane.

5. The speculum of claim 4, wherein said pair of projections comprises first and second projections and said pair of cups comprises first and second cups, wherein said first projection is coupled with said first cup and said second projection is coupled with said second cup, and wherein said cup plane bisecting said first cup is aligned with said projection plane bisecting said first projection and said cup plane bisecting said second cup is aligned with said projection plane bisecting said second projection.

6. The speculum of claim 4, wherein each projection plane and each cup plane are generally perpendicular to said primary speculum plane.

7. The speculum of claim 1, wherein one of said cups is configured for positioning around an upper eyelid and the other of said cups is configured for positioning around a lower eyelid, and wherein said projections are configured for positioning said cups around the eyelids to expose a desired portion of the underlying eyeball.

8. The speculum of claim 7, wherein said arms comprise an elastic material, and wherein said cups are spaced a distance corresponding with a distance between the upper and lower eyelids that is desirable for performing a surgical procedure on the underlying eyeball.

9. The speculum of claim 8, wherein said cups are spaced a distance of approximately between 30 to 40 millimeters.

10. The speculum of claim 1, further comprising a tab coupled with said pair of arms.

11. The speculum of claim 10, wherein said tab extends downward at an angle from said pair of arms.

12. The speculum of claim 1, wherein each of said projections is rectangular.

13. An eyelid speculum, comprising:
an elastic, generally U-shaped frame comprising a top, a bottom and a pair of free ends, wherein said top is positioned in a primary speculum plane and said bottom is adapted to be adjacent the eyeball;
a pair of cups, each of said cups coupled with one of said free ends; and
a pair of projections, each of said projections coupled with one of said cups and extending primarily upward from said frame and substantially normal to the primary speculum plane.

14. The eyelid speculum of claim 13, wherein one of said cups is configured for positioning around an upper eyelid and the other of said cups is configured for positioning around a lower eyelid, and wherein said projections are configured for positioning said cups around the eyelids to expose a desired portion of the underlying eyeball.

15. The eyelid speculum of claim 14, wherein each of said projections is generally ring-shaped and is sized for receiving a human finger.

16. The eyelid speculum of claim 15, wherein each of said generally ring-shaped projections comprises an interior, generally annular surface.

17. The eyelid speculum of claim 15, wherein each of a pair of cup planes bisects one of said cups, wherein each of said cups comprises a generally U-shaped cross section when viewed in said bisecting cup plane, and wherein each cup plane is positioned at an angle to said primary speculum plane.

18. The eyelid speculum of claim 13, wherein each of said cups comprises an opening and each of said projections extends through said opening in one of said cups for coupling said projection with said cup.

19. The eyelid speculum of claim 13, wherein each of said projections is a rectangular plate.

20. A speculum for a user to manipulate the eyelids for exposing a portion of the eyeball, the speculum comprising:
a pair of arms, each arm having a free end and an opposing end, where the opposing ends are attached to one another;
a pair of cups, each cup coupled with a corresponding free end of one of said arms and placed within a primary speculum plane; and
a user manipulation element coupled with each cup and extending primarily upward and away from the primary speculum plane where the user manipulation element is adapted to receive a finger of the user.

* * * * *